United States Patent [19]

Müller-Schweinitzer

[11] 4,442,112
[45] Apr. 10, 1984

[54] DIHYDROPYRIDINE DERIVATIVES USEFUL IN TREATING VASCULAR HEADACHES

[75] Inventor: Else Müller-Schweinitzer, Oberdorf, Switzerland

[73] Assignee: Sandoz Ltd., Basel, Switzerland

[21] Appl. No.: 411,101

[22] Filed: Aug. 24, 1982

[30] Foreign Application Priority Data

Sep. 2, 1981 [GB] United Kingdom ................. 8126574

[51] Int. Cl.³ .................... A61U 31/44; A61U 31/445

[52] U.S. Cl. ..................................... 424/263; 424/267
[58] Field of Search ................................ 424/263, 267

Primary Examiner—Stanley J. Friedman
Attorney, Agent, or Firm—Gerald D. Sharkin; Robert S. Honor; Joseph J. Borovian

[57] ABSTRACT

A pharmaceutical composition for treating or preventing vascular headaches, containing a 4-(2,1,3-benz-oxa- or thia-diazolyl)-1,4-dihydropyridine as an active compound.

12 Claims, No Drawings

DIHYDROPYRIDINE DERIVATIVES USEFUL IN TREATING VASCULAR HEADACHES

The present invention relates to a novel pharmaceutical use of dihydropyridine derivatives of formula I

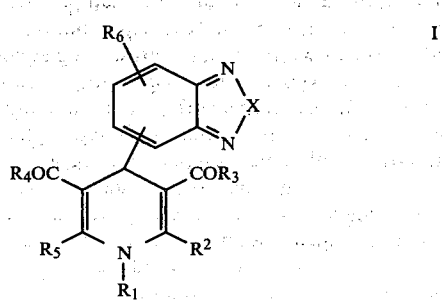

wherein
$R_1$ is hydrogen, alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, phenylalkyl of 7 to 9 carbon atoms or phenylalkenyl of 9 to 12 carbon atoms, the phenyl ring being unsubstituted or mono-, di- or trisubstituted independently by halogen, hydroxy or alkyl or alkoxy of 1 to 4 carbon atoms, $R_2$ and $R_5$, independently, are hydrogen or alkyl of 1 to 6 carbon atoms, $R_3$ and $R_4$, independently, are alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, alkoxy of 1 to 6 carbon atoms, hydroxyalkoxy of 2 to 6 carbon atoms, alkoxyalkoxy of 3 to 6 carbon atoms, hydroxyalkoxyalkoxy of 4 to 8 carbon atoms, alkenyloxy or alkinyloxy of 3 to 6 carbon atoms, cycloalkyloxy of 3 to 7 carbon atoms or cycloalkylalkoxy of 4 to 8 carbon atoms, $R_6$ is hydrogen, halogen, alkyl or alkoxy or alkylthio or alkylsulfonyl, each of 1 to 4 carbon atoms, trifluoromethyl, nitro or hydroxy, and X is oxygen or sulphur.

Certain pharmacological activities of the compounds of formula I have been published.

European Patent specification No. 150 discloses the blood pressure lowering activity of the compounds on the Grollman rat test as indicative of anti-hypertensive activity. It also discloses the increase in coronary blood flow and dilation of coronary vessels induced by the compounds in the cat. The compounds are therefore indicated for use in the treatment of coronary insufficiency.

Belgian Pat. No. 886,259 discloses that the compounds of formula I inhibit calcium induced contractions of isolated dog coronary arteries and are therefore indicated for use as spasmolytic agents, e.g. for the treatment of cholic. This Belgian patent also discloses that the compounds increase cerebral blood flow in the anaesthetized as indicated by the microsphere method and as indicated by a shortening in the post-ischemic recovery time in the isolated rat head after administration into the cartoid canula. These compounds are therefore indicated for use in the treatment of cerebrovascular insufficiency, cerebrovascular insults, cerebral vasospasms and stroke.

Pharmacological properties of 4-(2,1,3-Benzoxadiazol-4-yl)-1,4-dihydro-3-methoxycarbonyl-2,6-dimethyl-5-pyridinecarboxylic acid methylester (PY) have been reported by R. Hof. et al. in Brit. J. Pharmacol. 73, 196P, (1981) wherein is disclosed that the compound in an anaesthetized open chest cat decreases the blood pressure and the heart rate and increases the cardiac output and coronary flow.

In regional blood flow tests the drug increases myocardial flow and redistributed it in favour of the outer layer of the left ventricle and increases substantially the blood flow to the kidneys.

We have now found that the compounds of formula I, in particular the compound 4-(2,1,3-benzothiadiazol-4-yl)-2,6-dimethyl-1,4-dihydro-pyridine-3,5-carboxylic acid dimethyl ester, hereinafter referred to as compound A, surprisingly possess a combination of properties which make the compounds useful for the treatment of vascular headaches and which are nowhere suggested by the published pharmacological activities of the compounds, as follows:

(1) a dose-dependent reduction of arteriovenous shunted blood flow in the cartoid area, and (2) a dose-dependent antagonism of serotonin induced vasoconstriction of the basiliar artery at doses significantly lower than those which antagonize serotonin induced vasoconstriction of the peripheral mesenteric artery.

The reduction of arteriovenous shunted blood flow is observed as follows.

In one test in the cartoid area in cats under choralose-/urethane anesthesia, measured after administration of the active substance and after injection of microspheres into the Arteria lingualis (method described by R. P. Hof et al. in Basic Res. Cardiol. 75, 1980, p. 747–756).

A significant reduction in shunted blood flow is observed on sub-lingual administration of from about 20, especially from 40 to 240 µg/kg animal body weight of the compounds.

For the compound A at a dose of 120 µg/kg on sublingual administration the shunted blood flow was found to be reduced by 31% and by 37%, 15 and 60 minutes, respectively, after administration.

Blood pressure and heart frequency are hardly influenced at a dose of 44 µg/kg i.v.

In a second test the reduction in arteriovenous shunting is observed by an increase in the arteriovenous $O_2$ saturation difference between the carotid artery and jugular vein in the carotid area in the normotensive anaesthetized dog. The increase is observed on administration i.v. of from about 10 to about 100 µg/kg animal body weight of the compounds.

For compound A at a dose of 100 µg/kg i.v. the $O_2$ saturation difference was found to be 21.0% (control value 15.4%).

The selective antagonism of the serotonin induced vasoconstriction of the basiliar artery is observed as follows.

The compounds of formula I antagonize the serotonin (5-HT) induced contraction of isolated spiral strips of canine basiliar artery at concentrations from 10 to 1000 nM/1 according to the method described by E. Müller-Schweinitzer, Naunyn-Schmiedeberg's Arch. Pharmacol. 292, 113–118 (1976).

In basiliar arterial strips from dogs compound A caused a dose dependent depression of the maximum response to serotonin indicating non-competitive antagonism. A $pD_2'$ (30 min) value which is of 7.2 was determined for the compound A against serotonin. $PD_2'$ is the negative logarithm of the molar concentration, which causes a 50 percent inhibition of the maximal serotonin vasoconstricting effect. The antagonism of the peripheral mesenteric artery may be observed using strips of canine arteries at a higher dosage than that required for antagonism on basiliar artery. With compound A the effects were antagonised non-competitively. The maximal effect of serotonin is only reduced by 45% at 10 μM. A $pD_2'$ (30 min) value on the mesenteric artery of 6.2 was determined, which means that the compatability of compound A for antagonising serotonin effects on the basiliar artery is ten times that for antagonising serotonin effects on the mesenteric artery.

The tolerability (side effects) of the compounds is also studied using standard tests. For example in the case of compound A on administration of 2 mg/kg i.v. to anaesthetized dogs was well tolerated. The other compounds of formula I are equally well tolerated.

The compounds of formula I are therefore useful for the treatment of vascular headaches. The present invention accordingly provides in one aspect a method for treating vascular headaches which comprises administering a compound of formula I to a subject in need of such treatment. In another aspect the invention provides a composition for use in the treatment of vascular headache. Vascular headaches that may be treated include migraine and cluster headaches. The compounds may be administered to treat headaches already present, i.e. acute therapy or to prevent the occurence of headaches i.e. interval therapy.

For the treatment of vascular headaches, the exact dosage will of course vary depending on the compound employed, the mode of administration and therapy desired. However, in general, satisfactory results are obtained with a daily dosage of from about 3 μg/kg to about 5 mg/kg i.v., especially from about 10 μg/kg to about 1 mg/kg animal body weight conveniently administered in divided doses, e.g. 2 to 4 times a day, or in sustained release form. For the larger mammal, a daily dosage of from about 0.2 to about 350 mg, preferably 1 to 70 mg, especially 1 to 10 mg i.v., and from about 30 to 2000 mg per os or from about 3 to about 200 mg sublingually for interval therapy. Especially for interval therapy the unit dosage may be administered in divided dosages e.g. 3 times a day containing from about 0.1 to about 150 mg i.v. or about 10 to about 700 mg per os or about 1 to about 70 mg sublingually of the compound admixed with a solid pharmaceutical carrier or diluent.

For the acute therapy sub-lingual administration of a unit dosage form may contain e.g, from about 10 to about 50 mg, of the compound administered with a solid or liquid pharmaceutical diluent or carrier.

The compounds of formula I may be administered in similar manner to known standards for use in the treatment of vascular headache, e.g. Flunarizin. The suitable daily dosage for a particular compound will depend on a number of factors such as its relative potency of activity. It has for example been determined that the preferred compound of the present invention compound A, is 10 times more potent in antagonising serotonin in canine basiliar arteries than Flunarizin, which is effective for the treatment of migraine according to Medizinische Welt p. 1870–1872 (1980). Compound A may be administered at lower dosages as Flunarizin, especially if sub-lingually administered.

The compounds of formula I may be administered on their own or in the form of pharmaceutical compositions. Such compositions conveniently contain more than 1% by weight of the compound of formula I and may be prepared by conventional techniques to be in conventional forms, for example, capsules, tablets, suppositories, dispersible powders, suspensions, for enteral or parenteral administration. Suitable pharmaceutical diluents or carriers include, for example, alcohols, e.g. polyethylene glycol, polyvinylpyrrolidone, mannitol and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation.

It is preferred to use pharmaceutical compositions formulated to facilitate rapid absorption of a compound of formula I. For example oral pharmaceutical compositions may be employed and formulated to dissolve rapidly in the mouth, e.g., sub-lingual tablets and capsules. Alternatively the pharmaceutical compositions may be in powder or liquid form for adminstration as a spray or mist into the oral or nasal cavity.

It is contemplated that a spray applicator, e.g. an atomizer, may be used for administering such a spray or mist. Such spray applicators are known, for example atomizers for administering a liquid spray, and powder blowers which may be constructed to receive a cartridge containing a unit dosage of a liquid or powder pharmaceutical composition, break the cartridge, and expel the contents in the form of a spray or mist. Alternatively a pressurized container may incorporate a pharmaceutical composition in the form of a powder or liquid and compressed gas for expelling the compositions. Naturally metering devices may be incorporated to facilitate administration of a predetermined amount of the pharmaceutical composition.

All these devices and the techniques used for formulating suitable pharmaceutical compositions are well known.

In a further aspect the present invention provides a pack or dispenser device containing a compound of formula I, e.g., in the form of a pharmaceutical composition, for treatment of vascular headache. The pack or dispenser device may contain a plurality of unit dosage forms containing a compound of formula I. These may be packed in metal or plastic foil, e.g. as a blister pack. The pack or dispenser may be provided with instructions for administration of a compound of formula I in the treatment of vascular headache.

The following Examples are illustrative of compositions for use in the invention.

EXAMPLE 1

Hard gelatine capsules for oral administration

Hard gelatine capsules containing the ingredients indicated below may be prepared by conventional techniques, and be administered once a day for the treatment of vascular headaches.

| Ingredient | Weight |
|---|---|
| Compound A | 10.0 mg |
| Polyvinylpyrrolidone | 30.0 mg |
| Lactose | 148.5 mg |

-continued

| Ingredient | Weight |
| --- | --- |
| Corn starch | 60.0 mg |
| Magnesium stearate | 1.5 mg |
| | 250.0 mg |

EXAMPLE 2

Tablets for sublingual administration

| Ingredient | Weight |
| --- | --- |
| Compound A | 10.0 mg |
| Polyethyleneglycol 6000 | 33.0 mg |
| Mannitol | 50.0 mg |
| Polyvinylpyrrolidone | 4.5 mg |
| Talc | 2.0 mg |
| Magnesium stearate | 0.5 mg |
| | 100.0 mg |

EXAMPLE 3

Soft gelatine capsules for sublingual administration

| Ingredient | Weight |
| --- | --- |
| Compound A | 10.0 mg |
| Polyethyleneglycol 2000 | 100.0 mg |
| Polyethyleneglycol 400 | 140.0 mg |
| | 250.0 mg |

Sufficient amounts of the above components are mixed in conventional manner and filled into gelatine capsules or compressed to tablets, which are administered once a day for the treatment of vascular headaches.

What we claim is:

1. A method for treating or preventing vascular headaches, which comprises administering a therapeutically effective amount of a compound of formula I.

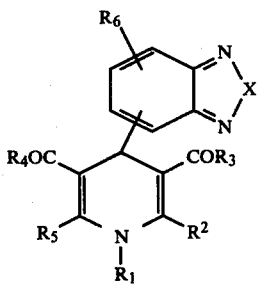

I wherein
$R_1$ is hydrogen, alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, phenylalkyl of 7 to 9 carbon atoms or phenylalkenyl or 9 to 12 carbon atoms, the phenyl ring being unsubstituted or mono-, di- or trisubstituted independently by halogen, hydroxy or alkyl or alkoxy of 1 to 4 carbon atoms.

$R_2$ and $R_5$, independently, are hydrogen or alkyl of 1 to 6 carbon atoms, $R_3$ and $R_4$, independently, are alkyl of 1 to 6 carbon atoms, alkenyl or alkinyl of 3 to 6 carbon atoms, cycloalkyl of 3 to 7 carbon atoms, cycloalkylalkyl of 4 to 8 carbon atoms, alkoxy of 1 to 6 carbon atoms, hydroxyalkoxy of 2 to 6 carbon atoms, alkoxyalkoxy of 3 to 6 carbon atoms, hydroxyalkoxyalkoxy of 4 to 8 carbon atoms, alkenyloxy or alkinyloxy of 3 to 6 carbon atoms, cycloalkyloxy of 3 to 7 carbon atoms or cycloalkylalkoxy of 4 to 8 carbon atoms, $R_6$ is hydrogen, halogen, alkyl or alkoxy or alkylthio or alkylsulfonyl, each of 1 to 4 carbon atoms, trifluoromethyl, nitro or hydroxy, and X is oxygen or sulphur, to a subject in need of such treatment.

2. A method according to claim 1 wherein the compound is 4-(2,1,3-benzothiadiazol-4-yl)-2,6-dimethyl-1,4-dihydropyridine-3,5-dicarboxylic acid dimethyl ester.

3. A method according to claim 1 wherein the compound is used in the treatment of migraine.

4. A method according to claim 1 wherein the compound is used in the treatment of cluster headache.

5. A method according to claim 1 wherein the compound is used for treating headaches already present.

6. A method according to claim 1 wherein the compound is used for preventing headaches.

7. A method according to claim 1 wherein the compound is administered sub-lingually.

8. A method according to claim 1 wherein the compound is administered perorally, 9. A method according to claim 1 wherein from 10 to 50 mg of the compound is administered sublingually for the treatment of headaches already present.

10. A method according to claim 1 wherein from 30 to 2000 mg per os or from 3 to 200 mg sublingually of the compound is administered daily for the prophylaxis of headaches.

11. A method according to claim 1 wherein the compound is administered in unit dosage form.

12. A method of claim 1, wherein the compound is administered in unit dosage form from 10 to 50 mg daily.

* * * * *